United States Patent [19]

Handke

[11] Patent Number: 4,869,299

[45] Date of Patent: Sep. 26, 1989

[54] RADIOACTIVITY SHIELDING TRANSPORTATION ASSEMBLY AND METHOD

[75] Inventor: Wayne A. Handke, Duncan, Okla.

[73] Assignee: Halliburton Company, Duncan, Okla.

[21] Appl. No.: 257,161

[22] Filed: Oct. 11, 1988

Related U.S. Application Data

[60] Continuation-in-part of Ser. No. 8,213, Jan. 28, 1987, abandoned, which is a division of Ser. No. 823,876, Jan. 29, 1986, abandoned.

[51] Int. Cl.[4] .......................... B65B 3/04; A61N 5/12; G21F 5/00

[52] U.S. Cl. .......................................... 141/1; 141/2; 141/27; 141/97; 141/98; 141/311 R; 141/329; 220/DIG. 21; 250/506.1; 600/1; 206/438; 604/905

[58] Field of Search .......................... 141/1, 2, 25–27, 141/97, 311 R, 329, 330, 365, 366, 98; 220/DIG. 21, 400, 402; 206/527, 438; 222/386; 250/506.1, 507.1; 600/1–5, 7; 604/415, 403, 905

[56] References Cited

U.S. PATENT DOCUMENTS

| | | | |
|---|---|---|---|
| 2,571,302 | 10/1951 | Smith | 141/97 |
| 3,330,281 | 7/1967 | Visser | 141/27 X |
| 3,330,282 | 7/1967 | Visser et al. | 141/27 X |
| 3,336,924 | 8/1967 | Sarnoff et al. | 604/415 |
| 3,432,666 | 3/1969 | Nash et al. | 206/527 X |
| 3,531,644 | 9/1970 | Koster | 250/506.1 |
| 3,552,387 | 1/1971 | Stevens | 604/88 |
| 3,655,985 | 4/1972 | Brown et al. | 128/1.1 |
| 3,729,031 | 4/1973 | Baldwin | 141/2 |
| 4,092,546 | 5/1978 | Larrabee | 250/506.1 |
| 4,122,836 | 10/1978 | Burnett | 600/5 |
| 4,401,108 | 8/1983 | Galkin | 600/5 |
| 4,497,349 | 2/1985 | Farley | 128/1.1 |
| 4,576,211 | 3/1986 | Valentini et al. | 141/329 |
| 4,625,122 | 11/1986 | Botzem et al. | 250/506.1 |

*Primary Examiner*—Ernest G. Cusick
*Attorney, Agent, or Firm*—Mark E. McBurney; E. Harrison Gilbert, III

[57] ABSTRACT

A method of transferring radioactive substance wherein a radioactivity shielding assembly, suitable for transferring a radioactive substance with a reduced risk of human exposure and environmental contamination, includes a protective shield casing having a reservoir disposed in the casing for receiving the radioactive substance. Associated with the casing is a coupling structure for coupling the reservoir and casing directly to a receiver into which the radioactive substance is to be transferred. The casing includes a side shielding structure in which the reservoir is retained and two end shield structures which are removably attached to the side shield structure. The two end shield structures are removed from the side shield structure at the location at which the radioactive substance is to be discharged, but such removal leaves the reservoir protectively received in the side structure to maintain continued protection against radioactive exposure or contamination.

6 Claims, 3 Drawing Sheets

RADIOACTIVITY SHIELDING TRANSPORTATION ASSEMBLY AND METHOD

This application is continuation, of application Ser. No. 008,213, filed 1/28/87, which is a divisional of application Ser. No. 823,876, filed 1/29/86, both abandoned.

BACKGROUND OF THE INVENTION

This invention relates generally to a protective assembly in which a radioactive substance can be transferred and a related method of so transferring the substance and more particularly, but not by way of limitation, to a radio-activity shielding container and method of using the same in transferring a radioactive substance directly to a receiver without substantially disassembling the container.

In the medical industry liquid radioactive tracer substances are used for various purposes. Such tracers are often transported in receptacles which are packaged to provide some degree of radioactivity shielding. In the oil industry, particulate radioactive tracer substances have been used in fracturing activities to detect where fractures have been made. At the present time, liquid radioactive tracer substances are also being used in the oil industry for a similar purpose.

Some advantages of using such liquid tracers in the oil industry are that the tracers can be pumped directly into the well at high pressures with conventional pumping equipment, the tracers can be accurately volumetrically metered, and the tracers can be shipped in concentrated forms so that small shipping packages can be used.

These usages, both in the medical and oil industries, bring people, equipment and the surrounding environment into association with, and thus into potential exposure to and contamination from, the radioactive substances, which substances can be very absorbent in liquid form and which substances can have large radiation exposure levels associated with small amounts in concentrated form. Furthermore, the used packaging, which can have a significant residue of the tracer or otherwise be contaminated, can also provide a health risk if it is not properly constructed and handled. In view of these risks of radiation exposure and contamination, the packaging in which such substances are transported from their points of being charged with the radioactive substances to their points of being discharged of the substances must be carefully manufactured and handled. Depending upon the nature of the use to which the packaging is to be put, such packaging may even need to meet governmental regulations, such as of the type promulgated by the United States Department of Transportation.

Two types of packaging, one used in the medical industry and the other used in the oil industry, are known to me. One type includes a syringe body which is concentrically received within a removable cylindrical lead jacket. This syringe body and jacket are placed in a carrying housing having a removable cap which is used to close the open end of the housing once the syringe and jacket assembly are placed inside the housing.

A shortcoming of this type of packaging is that the syringe body, which is made of a material that does not provide any significant radioactivity shielding, can be easily separated from the protective cylindrical sleeve during use. Furthermore, the syringe body, even if it is not removed from the protective sleeve, must be handled during use to remove it from the outer housing after the cap is removed from the housing. One also needs to handle the syringe body in connecting it to the object into which the radioactive substance is to be transferred.

The other type of packaging of which I am aware includes a lead carrying housing having a cavity into which a glass bottle, filled with the radioactive substance, is received. The glass bottle has a screw-on cap associated with it, and the carrying housing has a suitable lid associated with it. This type of packaging is potentially more hazardous than the previously mentioned packaging because it has no protective sleeve surrounding the bottle once it is removed from the lead housing, and such removal is necessary in pouring the radioactive substance from the bottle. This requires that a person either directly handle the unshielded bottle in removing it from the housing and in removing its cap and pouring the substance from the bottle or indirectly handle the bottle through some type of mechanical manipulating device, which type of device is likely less sensitive in its control of the bottle than direct human handling would provide, whereby the contents of the bottle can be easily and inadvertently spilled. Furthermore, such mechanical manipulation devices are not always available at well site where radioactive tracer is to be transferred for injection into a well during a fracturing process, for example.

In view of the foregoing shortcomings of these two prior art containers known to me, there is the need for a durable safety container which is constructed and used in such a way that inadvertent or unnecessary radioactivity exposure or contamination of humans, equipment and the environment can be avoided or minimized. Such a container should provide a receptacle for receiving the radioactive substance and a protective casing which is not to be separated from the receptacle during normal usage. Such a container should be designed so that minimal handling is required in either charging or discharging a radioactive substance into or out of the container. Such a construction minimizes the risk of exposure or contamination of personnel, equipment and the environment. Such a container should be constructed of components that can be easily manufactured in compliance with pertinent governmental regulations, such as those promulgated by the Department of Transportation. There is also the need for an associated method of safely transferring a radioactive substance with such a container.

SUMMARY OF THE INVENTION

The present invention overcomes the above-noted and other shortcomings of the prior art by providing a novel and improved radioactivity shielding transportation assembly and associated method of using the same. This assembly provides a container which is constructed so that at most only end caps are removed during usage of the assembly in either loading or unloading the radioactive substance into or from the container. This construction of the present invention avoids or minimizes inadvertent or unnecessary radiation exposure or contamination of personnel, equipment or the environment. Other than the end caps, no other components are separated during normal usage so that significant shielding is maintained at all times. The container is constructed so that it is readily connectible directly to a complementally constructed receiver into which the radioactive substance is to flow. The present invention can be easily manufactured so that it complies with pertinent governmental regulations. The present invention also provides an associated method of transferring a radioactive substance with such a container.

Broadly, the present invention provides a container in which a radioactive substance is transportable, such as to a location where the substance is to be moved into a receiver apparatus (e.g., to a well site where the radioactive substance is a liquid tracer to be injected into the well during a fracturing operation). The container comprises reservoir means for holding the radioactive substance; casing means, having the reservoir means disposed therein, for providing a radiation shield about the reservoir means; and coupling means for coupling the reservoir means and the casing means directly to the receiver apparatus. In a preferred embodiment, the casing means includes side shield means, having the reservoir means disposed therein, for blocking radioactivity from passing beyond the side shield means; top end shield means, directly releasably connected to the side shield means, for blocking radioactivity from passing beyond the top end shield means; and bottom end shield means, directly releasably connected to the side shield means, for blocking radioactivity from passing beyond the bottom end shield means. In the preferred embodiment, the side shield means includes a body, a portion of which forms an alignment portion defining the coupling means.

In accordance with the method of the present invention, a radioactive substance can be safely transferred by performing the steps of moving the radioactive substance into a reservoir housed within a protective radioactivity shielding container; transporting the container, having the radioactive substance stored therein, to a receiver into which the radioactive substance is to be transferred; mounting the container on the receiver; and moving the radioactive substance from the reservoir into the receiver without removing the reservoir from the container.

Therefore, from the foregoing, it is a general object of the present invention to provide a novel and improved radioactivity shielding transportation assembly and associated method. Other and further objects, features and advantages of the present invention will be readily apparent to those skilled in the art when the following description of the preferred embodiments is read in conjunction with the accompanying drawings.

DETAILED DESCRIPTION OF THE PREFERRED EMBODIMENTS

Figure 1:
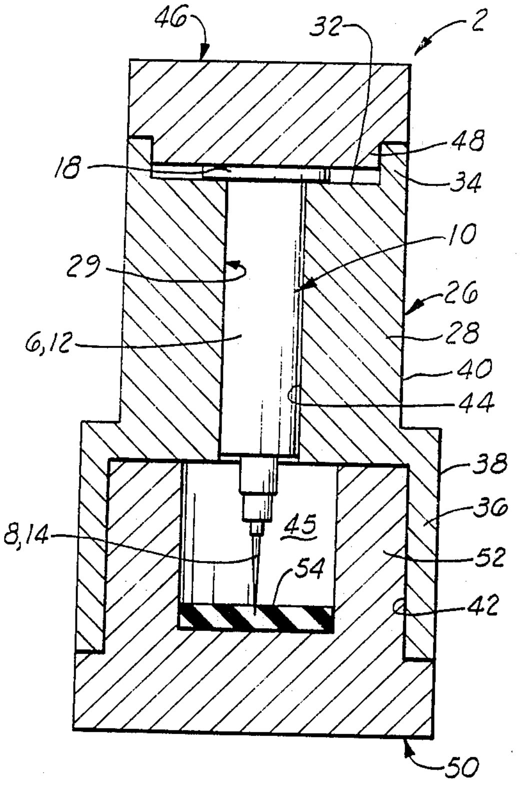
FIG. 1 is a sectional elevational view of a first preferred embodiment of the container of the present invention.

Depicted in the drawings are two embodiments of an assembly constructed in accordance with the present invention. The assembly of each of these embodiments is generally referred to and identified as a container 2 specifically adapted for transferring liquid radioactive substances to a receiver 4 [see FIGS. 9(*e*) and (*f*)]. In one specific contemplated use, the receiver 4 is a well head connection or a mixing vessel found at, or transportable to, a well site. Such a receiver 4 receives the radioactive substance and a diluting fluid for blending with the radioactive substance prior to injection of the blend into the well for use in tracing fractures in a formation of the well (an example of such a receiver is shown in a co-pending United States patent application entitled "Multiple Reservoir Transportation Assembly for Radioactive Substances, and Related Method" and assigned to the assignee of the present invention). Although the following description of these preferred embodiments will be made with reference to such usage in the oil industry, the present invention is not limited to such usage; rather, it is contemplated that the present invention can be constructed for use with radioactive substances other than liquids and for applications other than in the oil industry.

Broadly, the container 2 includes reservoir means for holding the radioactive substance; casing means, having the reservoir means disposed therein, for providing a radiation shield about the reservoir means, and coupling means for coupling the reservoir means and the casing means directly to the receiver apparatus. The casing means more particularly includes side shield means, having the reservoir means disposed therein, for blocking radioactivity from passing beyond the side shield means; top end shield means, directly releasably connected to the side shield means, for blocking radioactivity from passing beyond the top end shield means; and bottom end shield means, directly releasably connected to the side shield means, for blocking radioactivity from passing beyond the bottom end shield means. Each of these components of the assembly of the present invention will be more particularly described hereinbelow with reference to the first embodiment shown in FIG. 1 and the second embodiment shown in FIG. 2. The method of using the assembly or container 2 of the present invention will be described with reference to FIGS. 8A, 8B and 9(*a*)–(*j*).

The reservoir means of the first embodiment shown in FIG. 1 includes an elongated receptacle 6 having a port member 8 extending axially therefrom. The receptacle 6 and the port member 8 are specifically embodied in the construction shown in FIG. 1 by a commercially available plastic syringe 10 having a syringe body 12 defining the receptacle 6 and further having a hollow needle 14 defining the port member 8. The syringe body 12 has a longitudinal chamber (of the type shown in FIG. 8A and identified by the reference numeral 16), which chamber has an open upper end and an open lower end in fluid communication with the hollow portion of the needle 14. The open upper end of the cavity is encircled by a flange 18 which supports the syringe 10 in the casing means of the container 2 as shown in FIG. 1.

Figure 8A:
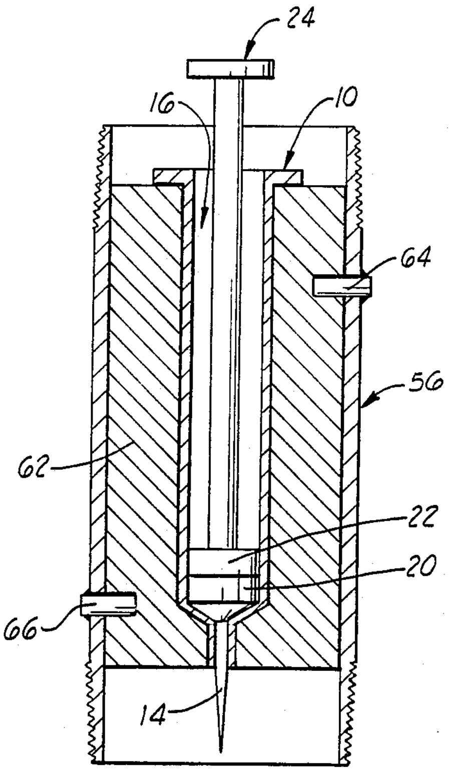
FIG. 8A is a sectional elevational view of the assembly shown in FIG. 2 having an unloaded syringe disposed therein.

In addition to the receptacle 6 and the port member 8, the reservoir means includes suitable means for ejecting the radioactive substance from the container 2. In the preferred embodiment shown in FIG. 1 (as well as for the embodiment shown in FIG. 2), this ejecting means includes a plug 20, having a tapered, frusto-conical lower end, to which plug 20 another plug 22 and a plunger rod 24 can be connected for slidingly moving the plug 20 through the cavity of the syringe 10. These elements are illustrated in FIG. 8A. In these embodiments, these elements also define a means for drawing the radioactive substance into the container 2, and specifically into the chamber 16 of the syringe 10, as will be more particularly described hereinbelow.

The syringe 10 defining the reservoir means of the FIG. 1 embodiment is retained in the side shield means of this embodiment, which side shield means is defined by an openended cylindrical container body 26. The body 26 has a central support portion or reservoir receiving portion comprising an annular wall 28 made of lead (or other suitable radiation shielding material). Extending longitudinally (specifically, axially) through the wall 28 is a cavity 29 in which the syringe body 12 is received. The top end of the cavity through the wall 28 terminates adjacent a shoulder portion 32, upwardly from which extends an annular rim 34 integrally formed with the wall 28. When the syringe 10 is disposed in the cavity 29 through the wall 28, the lower surface of the flange 18 abuts the shoulder surface 32 and the lower portion of the syringe 10 extends beyond the cavity 29.

The body 26 also integrally includes an annular wall 36 which is radially outwardly offset from the wall 28. An outer surface 38 of the wall 36 has a larger diameter than an outer surface 40 of the wall 28, and an inner surface 42 of the wall 36 has a larger diameter than an inner surface 44 of the wall 28 defining the longitudinal cavity 29. This inner surface 42 of the wall 36 defines a cavity 45 which communicates with the cavity 29 and into which the needle 14 extends. This disposition of the needle 14 is concentric or coaxial with the wall 36 in the FIG. 1 embodiment. This wall 36, although being physically a part of the body 26, defines the coupling means of the FIG. 1 embodiment and specifically provides an alignment portion or engagement portion with which the container 2 directly couples with the receiver, such as the receiver 4 schematically illustrated in FIG. 9. The wall 36 extends longitudinally from the wall 28 in a direction opposite the direction of extension of the rim 34 as is apparent in FIG. 1. The wall 36 extends from the wall 28 by a length which is greater than the length the needle 14 extends beyond the wall 28 so that the free end of the needle 14 does not extend beyond the lower perimeter of the wall 36.

To protectively close the two open ends of the container body 26, the container 2 includes the top and bottom end shield means. In FIG. 1, the top end shield means is defined by a cylindrical lead cap 46 having a lower protuberant portion 48 nesting within the rim 34 and having an area engaging the top of the flange 18 to retain the syringe 10 securely against the side shield means. The engagement between the cap 46 and the rim 34 can be by any suitable means, such as by threaded coupling or frictional engagement or otherwise, which provides an adequate retaining force so that the cap 46 cannot be inadvertently removed or knocked from the side shield means. This provides a suitable closure means for closing the top of the container 2 in a manner by which radioactivity is shielded or otherwise prevented from passing from beyond the top of the container 2.

The bottom end shield means of the FIG. 1 embodiment includes a cylindrical lead cap 50 having an annular wall 52 extending into the cavity 45, around the central region thereof into which the needle 14 extends, when the cap 50 is suitably attached to the alignment or engagement wall 38 as shown in FIG. 1. The wall 52 has an outer diameter substantially the same as the diameter of the inner surface 42 of the wall 36, and the wall 52 suitably couples therewith through a suitable retention force whereby the cap 50 will not be inadvertently removed from the container 2.

Disposed in the bottom of the cavity defined by the annular wall 52 of the cap 50 is a suitable support means, such as a rubber cushion 54, into which the free end of the needle 14 is received when the cap 50 is attached to the remainder of the container 2. This provides support for the needle 14 during transportation. The cap 50, being constructed of lead (or other suitable radioactivity shielding material), provides suitable radioactivity shielding.

Figure 2:
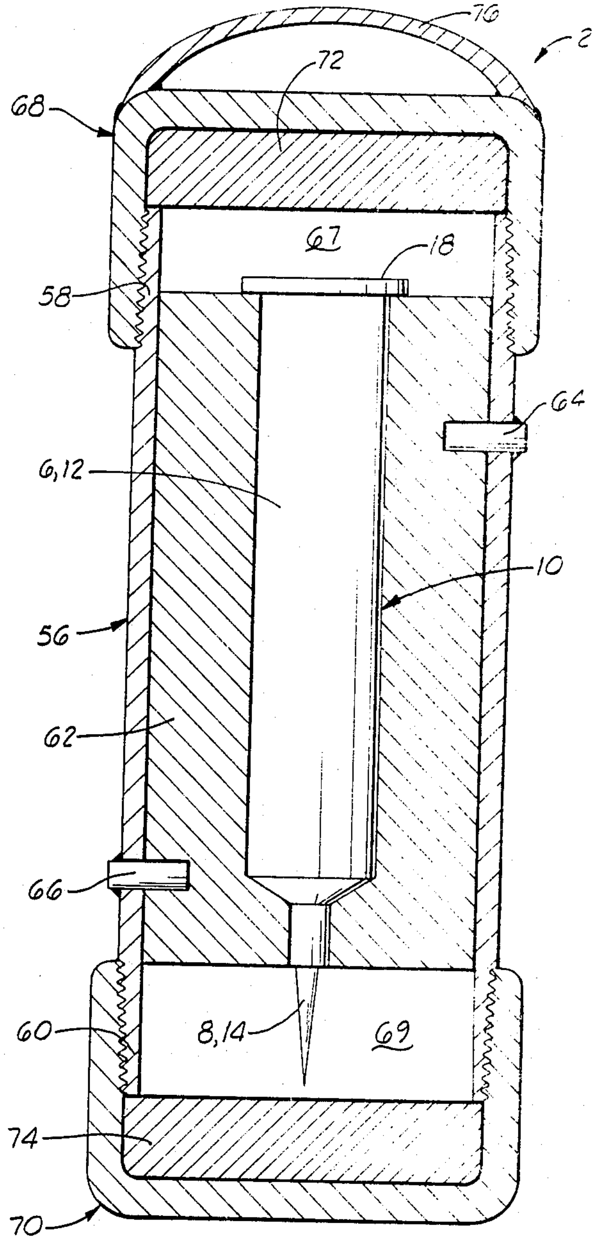
FIG. 2 is a sectional elevational view of a second preferred embodiment of the container of the present invention.

The second embodiment, which is depicted in FIG. 2, includes the same type of embodiment of the reservoir means as the FIG. 1 embodiment, as indicated by the like reference numerals used in identifying the syringe illustrated in FIG. 2. The side shield means of the FIG. 2 embodiment, however, is constructed differently.

The side shield means of this second embodiment includes a steel sleeve member 56 having two externally threaded end portions 58, 60. Although shown threaded in FIG. 2, these ends do not need to be threaded, but need to be constructed for suitably releasably securing with the top and bottom end shield means of this embodiment. Although the sleeve 56 has been identified as being constructed of steel, it may be constructed of any suitable material which provides adequate strength so that the container 2 can meet any applicable governmental regulations, such as those promulgated by the Department of Transportation.

Forming another part of the container body of the second side shield means embodiment is a radiation blocking member defined by a molded lead wall 62 having cavity defined therein suitable for receiving the syringe 10. The wall 62 is fastened to the sleeve 56 by radially extending pins 64, 66 protruding into the wall 62 and welded to the sleeve 56. As shown in FIG. 2, the wall 62 terminates short of the two extreme ends of the sleeve 56 to define suitable hollow regions 67, 69 in which the flange 18 and the needle 14 of the syringe 10 can be respectively accommodated.

The top and bottom end shield means of this second embodiment are constructed of suitable pipe caps 68, 70 adapted for coupling with the end portions 58, 60, respectively, of the sleeve 56. To provide radioactivity shielding in the caps, layers 72, 74 of lead are molded into the caps 68, 70, respectively. The cap 68 is shown with a handle 76 by which the container 2 can be conveniently carried or otherwise moved when the cap 68 is affixed to the sleeve 56.

Figure 9:
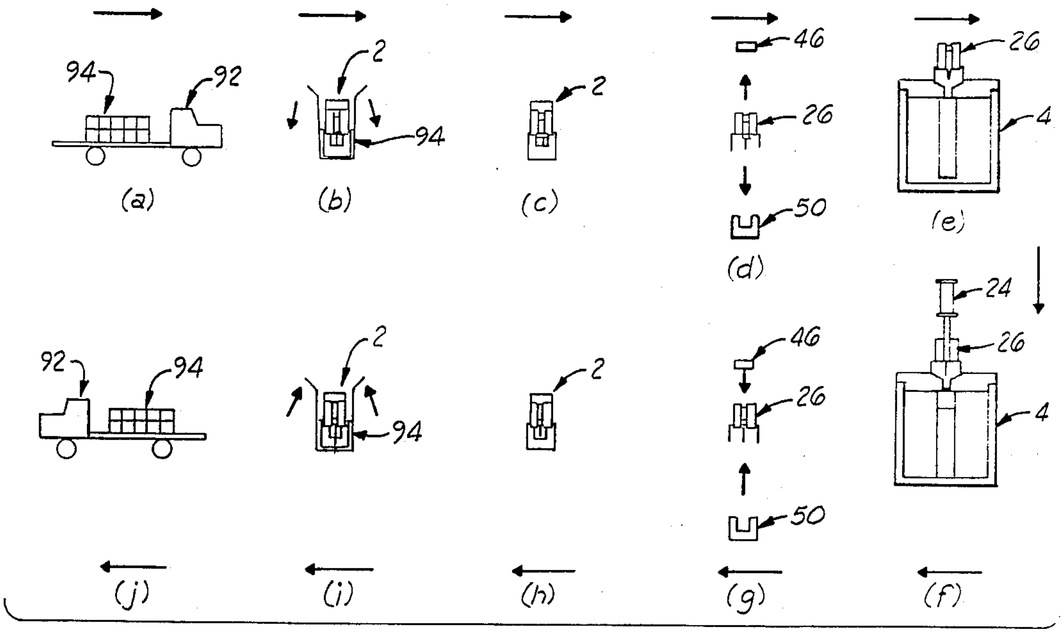
FIGS. 9(*a*)–(*j*) are schematic drawings depicting a preferred usage of the present invention.

The coupling means of the FIG. 2 embodiment is defined by the end portion 60 of the sleeve 56 whereby the end portion 60 mates with a complementally formed portion of the receiver, such as the receiver 4 depicted in FIG. 9.

Both of the embodiments shown in FIGS. 1 and 2 are designed for easy fabrication. As mentioned, the syringe 10 is commercially available and thus does not need to be specially manufactured. The elements of the casing means and the coupling means of the first preferred embodiment are readily molded using appropriately formed molds and molten lead or other suitable radioactivity shielding material. No maching or assembling of parts is thus necessary other than as is needed to fit the syringe into the axial cavity of the side shield means and to connect each of the end caps as shown in FIG. 1.

Figure 3:
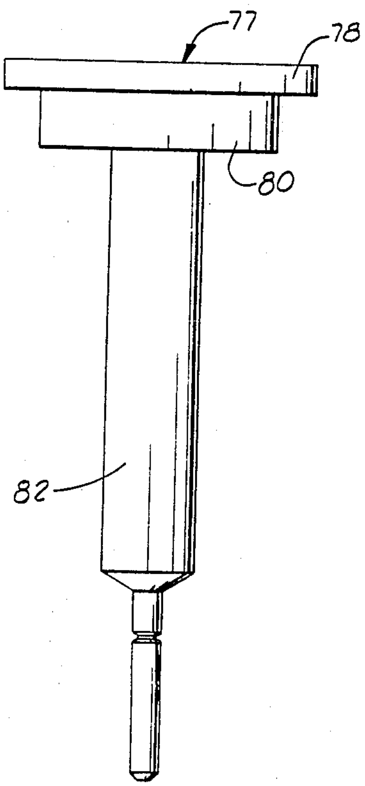
FIG. 3 is an elevational view of part of a mold for constructing the embodiment shown in FIG. 2.
Figure 4:
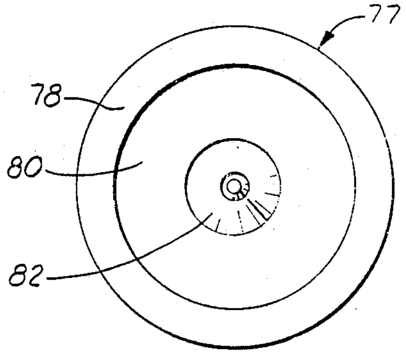
FIG. 4 is an end view of the mold shown in FIG. 3.

The embodiment of FIG. 2 is likewise easily manufactured. This embodiment is partially formed by using a twopiece mold of the type shown in FIGS. 3–6. FIGS. 3 and 4 show a mold piece 77 which comprises a base 78 from which a spacer 80 and a mandrel 82 extend.

Figure 5:
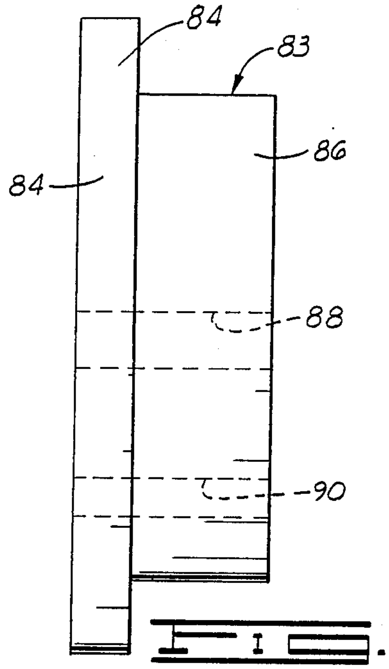
FIG. 5 is a side elevational view of another portion of the mold used in association with the portion shown in FIGS. 3 and 4.
Figure 6:
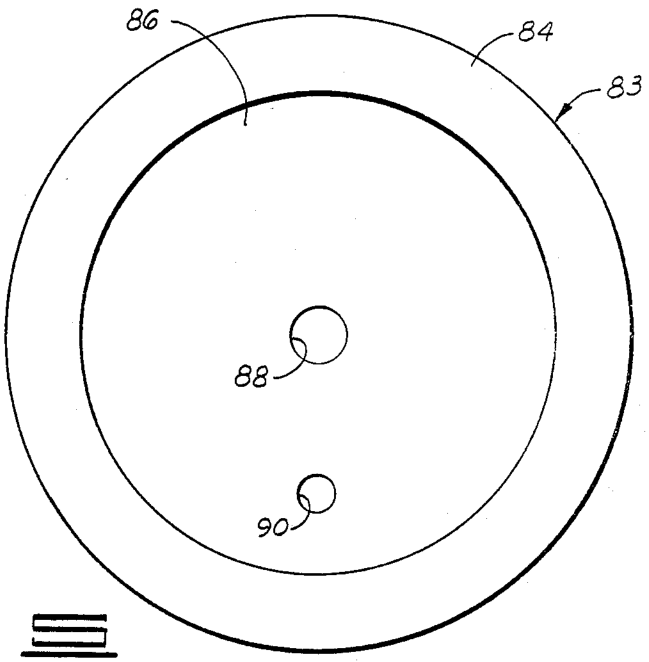
FIG. 6 is an end elevational view of the portion of the mold shown in FIG. 5.

Another mold piece, shown in FIGS. 5 and 6 and identified by the reference numeral 83, has a base 84 from which a spacer 86 extends. A central aperture 88 is defined for receiving the free end of the mandrel 82 when the two mold pieces 77, 83 are fitted together. The mold piece 83 shown in FIGS. 5 and 6 also includes a port 90 through which air is released when the mold pieces are positioned together.

Figure 7:
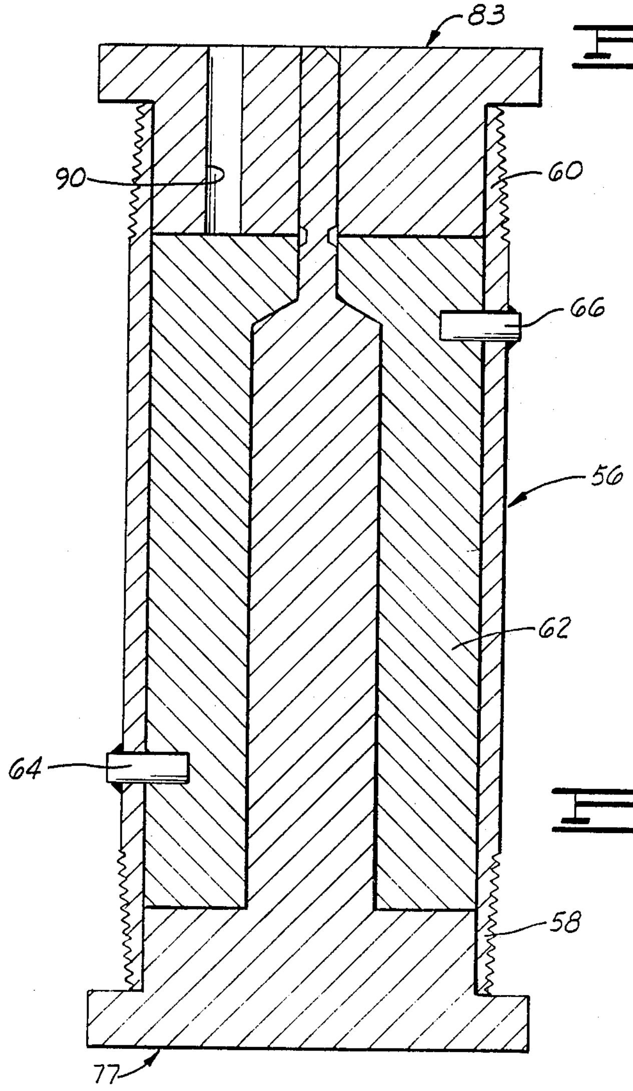
FIG. 7 is a sectional elevational view showing the mold assembled with a sleeve from which the embodiment shown in FIG. 2 is manufactured.

Such proper positioning of the mold pieces is illustrated in FIG. 7. First, the sleeve 56 is cut to the suitable length and its ends threaded or otherwise finished as necessary. The side holes through which the retaining pins 64, 66 are inserted are cut through the sleeve 56 and the pins 64, 66 are attached. The mold piece 77 is inserted through one end of the sleeve 56 as shown in FIG. 7, and molten lead, or other suitable radioactivity shielding material, is poured through the opposite end into the space between the sleeve 56 and the mold piece 77 up to the illustrated indentation formed in the thinner part of the mandrel 82. If needed or desired, the mold piece 83 is then inserted through this opposite end of the sleeve 56 so that the smaller diametered protuberant portion of the mandrel 82 is received in the central aperture 88 to maintain it in proper alignment: After the molten material has hardened to form the wall 62, the mold pieces 77, 83 are then removed. The molten shield material is also poured into the bottoms of the two caps 68, 70 to form the respective protective shielding layers shown in FIG. 2. To complete the assembly, the syringe 10 is inserted into the cavity vacated by the mandrel portion 82 and the two finished caps 68, 70 are affixed to their respective ends of the sleeve 56.

Figure 8B:
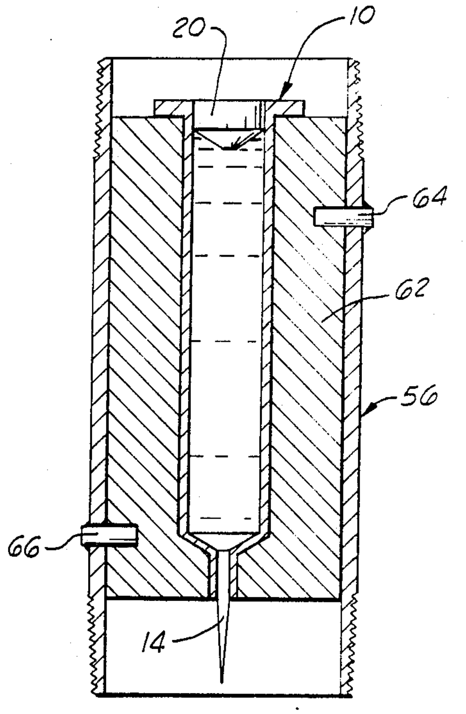
FIG. 8B is the same view as shown in FIG. 8A but with the syringe filled with radioactive substance.

Both of the described embodiments are used in a similar manner to transfer a radioactive substance from one location to another. With reference to FIGS. 8A and 8B, the method by which the container 2 is charged, or filled, with the radioactive substance (which will be described as a liquid tracer suitable for use in a fracturing fluid for the exemplary use of the container 2) will be described. In FIG. 8A, the plug 20 is shown at the bottom of the chamber 16 within the syringe 10. With the plug 20 positioned at such a location relatively close to the needle 14, the other plug 22 and the plunger rod 14 are inserted through the open end of the container 2, from which the top cap has been removed, and down into the empty chamber of the syringe 10. The container 2 is mounted on a suitable source of the radioactive tracer in a position where the free end of the needle 14 is immersed in the body of liquid tracer. The plunger rod 24 is then extracted or withdrawn upwardly, as viewed in FIG. 8A, away from the needle 14 whereby the coupled plugs 20, 22 are slid upwardly away from the former location of the plug 20 relatively near the needle 14 to a position farther from the needle 14. This step of sliding the plug is continued until the desired quantity of the radioactive substance is received in the chamber 16 of the syringe 10. If the chamber 16 is to be completely filled, the sliding step continues until the plug 20 is in the position shown in FIG. 8B, whereupon the plug 22 and the plunger rod 24 are detached from the plug 20, thereby leaving the plug 20 within the chamber 16 in sealing engagement with the syringe body to retain the radioactive substance therein. These steps accomplish the general step of moving the radioactive substance into the reservoir housed within the protective radioactivity shielding container 2.

Once the container 2 has been adequately filled, the container is transported, such as by a vehicle 92 illustrated in FIG. 9(*a*). In so transporting the container 2, it is customery to ship several identical containers in a packing carton of a suitable type, such as is schematically illustrated in FIG. 9(*b*) and identified by the reference numeral 94. When the container 2 reaches its destination, it is unpacked from the carton 94 as illustrated in FIG. 9(*c*). At this time, the container 2 can be manually handled, such as by a person using only protective gloves, since the radioactive substance is protectively housed within the fully assembled container 2.

In preparation for transferring the radioactive substance out of the container 2, the two end caps are removed as depicted in FIG. 9(*d*); however, it is to be noted that the syringe 10 remains fully retained in the side shield means from which the two end caps have been removed. This side shield means is then directly mounted on the reiceiver 4 in suitable alignment as established by the lower portion of the container body. This mounting is depicted in FIG. 9(*e*). In this position, the needle 14 is directly in communication with the region of the receiver into which the radioactive substance contained in the chamber 16 of the syringe body is to be transferred.

To complete the transfer, the plug 22 and plunger rod 24, or a similar structure, are connected to the plug 20 through the end from which the top cap has been removed. A downward force is applied to the plunger rod 24 to slide the plug 20 through the chamber of the syringe body toward the needle 14 so that the radioactive substance is ejected through the hollow channel defined through the needle 14. This is depicted in FIG. 9(*f*). Thus, the complete process of charging the container 2 with the radioactive substance and discharging the radioactive substance therefrom can be safely performed with minimal risk of human or equipment or environment exposure to, or contamination by, the radioactive substance.

Even after the radioactive substance has been discharged into the receiver, there is minimal risk of external contamination from the container 2 because the only components which have been in contact with the radioactive substance are the syringe body, the needle and the plug, all of which remain at all times housed at least within the side shield means. After the step of moving the radioactive substance from the reservoir of the container 2 into the receiver 4, these components are readily fully repackaged within the full container 2 by reattaching the two end caps [see FIG. 9(*g*)] to recomplete the assembly, as shown in FIG. 9(*h*). This reassembled container 2 is repackaged in the carton 94 and reloaded onto the vehicle 92 for safe return or disposal, as depicted in FIGS. 9(*i*) and (*j*).

From the foregoing, it is apparent that at no time is it necessary in the use of the present invention for the syringe containing the radioactive substance to be removed from the side shield body. As a result, any radiation exposure to an individual handling even the uncapped container 2 is intended to be low enough that the individual can safely handle the assembly with only gloved hands; however, it should be noted that as with any radioactive material, maximum safety precautions should be taken at all times. The present invention does, though, provide a convenient assembly by which a radioactive substance can be safely handled without using possibly clumsy remote-controlled tongs or other mechanical devices. Such mechanical devices, which are preferably used to handle the prior art screw-cap glass bottles, can be difficult to control so that there is a significant risk of spillage which could cause radioactive contamination. The present invention is also preferable to the lead-jacket-shielded prior art container used in the medical industry because the jacket of such container is easily removable and is not specifically adapted for both retaining the reservoir and simultaneously coupling with a receiver into which the radioactive substance is to be transferred.

Thus, the present invention is well adapted to carry out the objects and attain the ends and advantages mentioned above as well as those inherent therein. While preferred embodiments of the invention have been described for the purpose of this disclosure, numerous changes in the construction and arrangement of parts, and the performance of steps, can be made by those skilled in the art, which changes are encompassed within the spirit of this invention as defined by the appended claims.

What is claimed is:

1. A method of transferring a radioactive substance, comprising the steps of:

providing a syringe comprising a syringe body having a longitudinal chamber defined therein, a plug slidably disposed in said chamber and sealingly engaged therewith, and a hollow needle attached to the syringe body in communication with the chamber;

providing a protective radioactivity shielding container comprising a cylindrical body portion which houses said syringe, a first cap for enclosing the cylindrical body portion at an end opposite to said hollow needle, a second cap constructed from a single member for enclosing the cylindrical body portion at an end adjacent to said hollow needle, and a cushion portion disposed within said second cap;

moving the radioactive substance into said syringe housed within said protective radioactivity shielding container;

supporting the syringe within the container, said step of supporting comprises attaching said first cap to the end of said cylindrical body portion opposite said hollow needle, and attaching said second cap to the end of said cylindrical body portion adjacent said hollow needle such that said hollow needle is received by said cushion portion thereby providing support to said hollow needle;

transporting the container having the radioactive substance stored therein, over great distances to a receiver into which the radioactive substance is to be transferred;

mounting the container on the receiver; and moving the radioactive substance from said syringe into the receiver without removing said syringe from the container.

2. A method as defined in claim 1, wherein:

the step of moving the radioactive substance into the syringe includes:

positioning the container so that the needle is at least partially immersed into a source of the radioactive substance; and sliding the plug within the chamber from a position relatively closer to the needle to a position relatively farther from the needle until a desired quantity of the radioactive substance is received in the chamber.

3. A method as defined in claim 2, wherein the step of sliding the plug includes:

attaching another plug to the first-mentioned plug and attaching a plunger rod to the second-mentioned plug;

pulling the plunger rod until the first-mentioned plug is at the desired position; and detaching the plunger rod and the second-mentioned plug from the first-mentioned plug, leaving the first-mentioned plug within the chamber in sealing engagement with the syringe body.

4. A method as defined in claim 2, wherein the step of moving the radioactive substance from the syringe includes sliding the plug from the position relatively farther from the needle toward a position relatively closer to the needle.

5. A method as defined in claim 1, wherein:

the step of mounting the container on the receiver includes:

removing said second cap connected to the end of the cylindrical body portion adjacent said needle; and engaging the end of the cylindrical body portion, adjacent said needle, with the receiver so that the needle is in direct communication with the receiver.

6. A method as defined in claim 5, wherein the step of moving the radioactive substance from the syringe includes:

removing said first cap; and sliding the plug within the chamber from a position relatively farther away from the needle to a position relatively closer to the needle thereby ejecting the radioactive substance from the syringe through the hollow needle while the end of the cylindrical body portion adjacent the hollow needle engages the receiver.

* * * * *